US011786816B2

(12) United States Patent
Juenger et al.

(10) Patent No.: US 11,786,816 B2
(45) Date of Patent: Oct. 17, 2023

(54) SHARING MOVEMENT DATA

(71) Applicant: SONY INTERACTIVE ENTERTAINMENT LLC, San Mateo, CA (US)

(72) Inventors: Elizabeth Juenger, San Mateo, CA (US); Jennifer Sheldon, San Mateo, CA (US)

(73) Assignee: SONY INTERACTIVE ENTERTAINMENT LLC, San Mateo, CA (US)

( * ) Notice: Subject to any disclaimer, the term of this patent is extended or adjusted under 35 U.S.C. 154(b) by 75 days.

(21) Appl. No.: 17/390,372

(22) Filed: Jul. 30, 2021

(65) Prior Publication Data

US 2023/0029894 A1 Feb. 2, 2023

(51) Int. Cl.
*A63F 13/57* (2014.01)
*G06V 20/20* (2022.01)
*G06V 40/20* (2022.01)
*G06F 18/22* (2023.01)
*G06F 3/01* (2006.01)

(52) U.S. Cl.
CPC .............. *A63F 13/57* (2014.09); *G06F 3/017* (2013.01); *G06F 18/22* (2023.01); *G06V 20/20* (2022.01); *G06V 40/23* (2022.01)

(58) Field of Classification Search
CPC ........ A63F 13/57; G06V 20/20; G06V 40/23; G06F 18/22; G06F 3/017
USPC .......................................................... 463/31
See application file for complete search history.

(56) References Cited

U.S. PATENT DOCUMENTS

| 3,430,530 A |   | 3/1969 | Grindinger |   |
|---|---|---|---|---|
| 7,071,914 B1 |   | 7/2006 | Marks |   |
| 7,559,841 B2 |   | 7/2009 | Hasimoto |   |
| 8,284,157 B2 | * | 10/2012 | Markovic | G06F 3/017 715/706 |
| 8,412,662 B2 |   | 4/2013 | Ramic et al. |   |
| 8,427,508 B2 | * | 4/2013 | Mattila | H04W 4/023 345/634 |
| 9,089,775 B1 | * | 7/2015 | Daniel | A63F 13/65 |

(Continued)

FOREIGN PATENT DOCUMENTS

| CN | 115641421 | 1/2023 |
| CN | 115701082 | 2/2023 |

(Continued)

OTHER PUBLICATIONS

U.S. Appl. No. 17/389,083 Office Action dated Apr. 13, 2022.

(Continued)

*Primary Examiner* — Allen Chan
(74) *Attorney, Agent, or Firm* — POLSINELLI LLP

(57) ABSTRACT

Data captured during a movement by the user in a real-world environment may be received from a user device associated with a user. A corresponding movement is rendered by a virtual character within a virtual environment based on the data. Video of the corresponding movement within the virtual reality environment is captured and associated with the data. The captured video and the data are provided to a recipient designated by the user. It is then verified that the recipient is performing the movement by comparing data regarding the recipient during play of the captured video to the data associated with the captured video.

19 Claims, 5 Drawing Sheets

(56) References Cited

U.S. PATENT DOCUMENTS

| | | | |
|---|---|---|---|
| 9,350,951 B1* | 5/2016 | Rowe | G06T 7/66 |
| 9,358,456 B1 | 6/2016 | Challinor et al. | |
| 9,857,934 B2* | 1/2018 | Humphrey | G06F 3/0481 |
| 10,701,316 B1 | 6/2020 | Cheung et al. | |
| 11,049,321 B2* | 6/2021 | Lu Hill | G06T 7/246 |
| 2002/0160823 A1 | 10/2002 | Watabe et al. | |
| 2004/0161132 A1 | 8/2004 | Cohen et al. | |
| 2008/0096657 A1 | 4/2008 | Benoist | |
| 2008/0234023 A1 | 9/2008 | Mullahkhel et al. | |
| 2009/0163262 A1 | 6/2009 | Kang | |
| 2009/0325705 A1 | 12/2009 | Filer et al. | |
| 2010/0050133 A1 | 2/2010 | Nishihara et al. | |
| 2010/0306712 A1 | 12/2010 | Snook | |
| 2011/0093820 A1 | 4/2011 | Zhang | |
| 2013/0172070 A1 | 7/2013 | Kim et al. | |
| 2013/0176437 A1 | 7/2013 | Tseng | |
| 2013/0342571 A1 | 12/2013 | Kinnebrew et al. | |
| 2014/0108927 A1 | 4/2014 | Vaidya et al. | |
| 2014/0304665 A1 | 10/2014 | Holz | |
| 2015/0205359 A1 | 7/2015 | Feng et al. | |
| 2015/0347717 A1* | 12/2015 | Dalal | G16H 20/30 434/258 |
| 2016/0371888 A1 | 12/2016 | Wright et al. | |
| 2017/0103672 A1* | 4/2017 | Dey | G06F 3/011 |
| 2017/0228025 A1 | 8/2017 | Hall et al. | |
| 2018/0088671 A1 | 3/2018 | Wang | |
| 2018/0285062 A1 | 10/2018 | Ulaganathan et al. | |
| 2019/0130650 A1 | 5/2019 | Liu et al. | |
| 2020/0306640 A1 | 10/2020 | Kolen et al. | |
| 2020/0366960 A1 | 11/2020 | Quader et al. | |
| 2020/0381021 A1* | 12/2020 | Rothschild | G11B 27/10 |
| 2020/0393908 A1 | 12/2020 | Kejariwal | |
| 2021/0405763 A1 | 12/2021 | Liu et al. | |
| 2022/0121289 A1 | 4/2022 | Llamas et al. | |
| 2023/0051703 A1 | 2/2023 | Fortuna | |

FOREIGN PATENT DOCUMENTS

| | | | |
|---|---|---|---|
| CN | 115904060 | 4/2023 | |
| EP | 4 122 566 | 1/2023 | |
| EP | 4 137 916 | 2/2023 | |
| JP | 2023/016015 | 2/2023 | |
| JP | 2023-021047 | 2/2023 | |
| JP | 2023-027017 | 3/2023 | |
| KR | 2005-0082559 | 8/2005 | |
| WO | WO-2010001109 A2 * | 1/2010 | G06T 13/40 |

OTHER PUBLICATIONS

U.S. Appl. No. 17/403,242, Ellana Fortuna, Gesture-Based Skill Search, filed Aug. 16, 2021.

U.S. Appl. No. 17/389,083, Ellana Fortuna, Movement-Based Navigation, filed Jul. 29, 2021.

"Experience and Levels—Ring Fit Adventure Wiki Guide—IGN" May 7, 2020 [Retrieved from the Internet on Dec. 22, 2022] https://www.ign.com/wikis/ring-fit-adventure/Experience_and_Levels.

Miyoshi Maasa et al.; "Ring Fit Adventure" Wikipedia, Aug. 10, 2021 [Retrieved from the Internet on Dec. 20, 2022] https://en.wikipedia.org/w/index.php?title=Ring_Fit_Adventure&oldid=1038055950.

Nintendo of America: "Ring Fit Adventure Overview Trailer—Nintendo Switch" Aug. 31, 2020 [Retrieved from the Internet on Dec. 23, 2022] https://www.youtube.com/watch?v=skBNiJd61Qw.

European Application No. 22183803.0 Extended European Search Report dated Jan. 5, 2023.

European Application No. 22184797.3 Extended European Search Report dated Jan. 10, 2023.

European Application No. 22181663.0 Extended European Search Report dated Nov. 23, 2022.

U.S. Appl. No. 17/403,242 Office Action dated Nov. 4, 2022.

U.S. Appl. No. 17/403,242 Final Office Action dated Apr. 7, 2023.

* cited by examiner

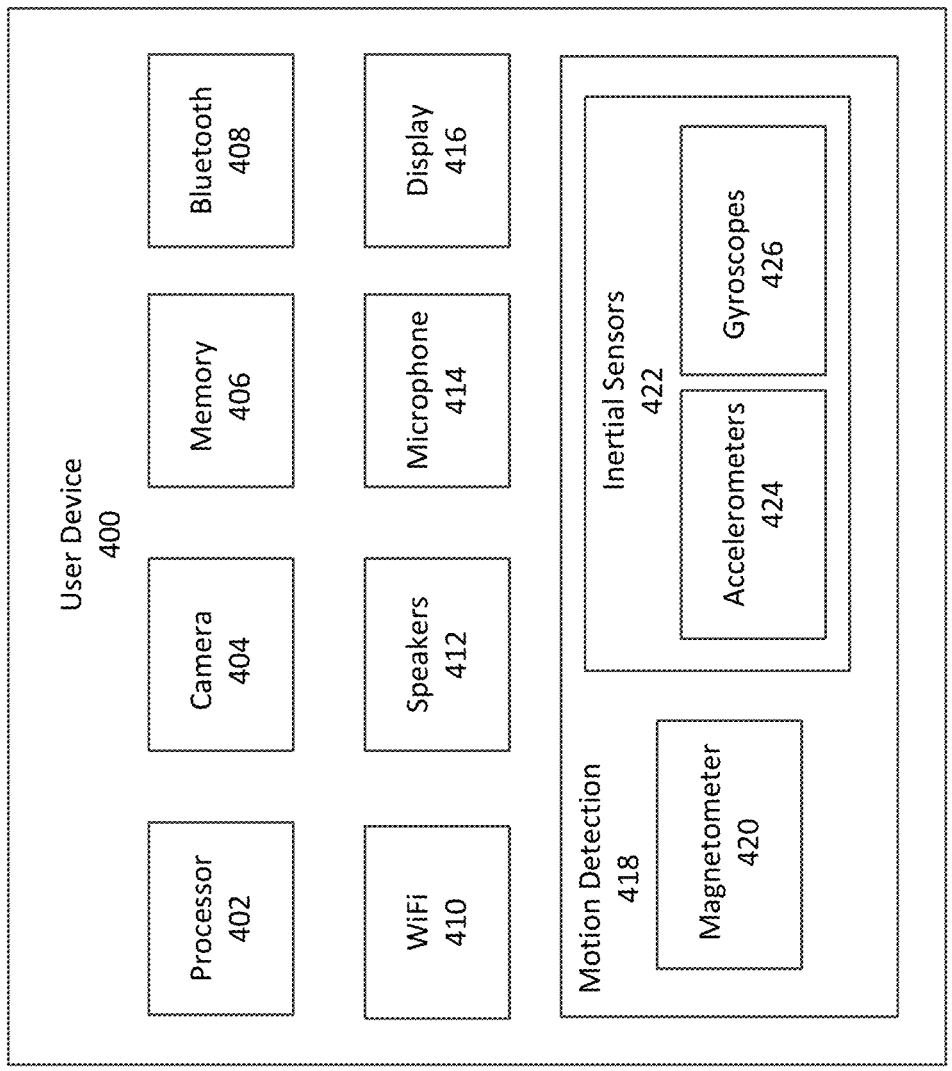
FIG. 4

SHARING MOVEMENT DATA

BACKGROUND OF THE INVENTION

1. Field of the Invention

The present invention generally relates to sharing movement data. More specifically, the present invention relates to capturing, analyzing, and sharing data regarding physical movement of a user.

2. DESCRIPTION OF THE RELATED ART

Presently available user devices include cameras that allow for capture of video, as well as sharing of such video through a variety of online social networks (e.g., TikTok®). The physical movement of a user may be characterized by more parameters, however, than can be captured by video alone. That is because video merely illustrates what the end result of the movement looks like. There is no analysis, for example, or any other type of data that might help a viewer understand the mechanics, rhythm, or force behind the movement or how to perform such movement correctly.

Various computing systems—such video game systems and other virtual reality systems—allow for reproduction of some elements of user movement within a virtual or otherwise digital environment. Such systems may rely on controllers and other sensors to capture movement data and to translate such movement data into instructions for controlling an avatar or character within the virtual environment. For example, certain gestural controls may be translated into different actions by the avatar in navigating and interacting with the virtual environment. While the avatar or character may be viewed by other users or players within the virtual environment, the underlying movement data characterizing the movement is not shared with others. Similar to camera-captured video, the viewer does not receive any movement analysis or instruction.

There is, therefore, a need in the art for improved systems and methods for capturing, analyzing, and sharing data regarding physical movement of a user.

SUMMARY OF THE CLAIMED INVENTION

Embodiments of the present invention include systems and methods for sharing movement data. A user device associated with a user is in communication with a content management server. The content management server receives data from the user device captured during a movement by the user in a real-world environment. The content management server renders a corresponding movement by a virtual character within a virtual environment based on the data. The content management server captures video of the corresponding movement within the virtual reality environment associated with the data. The content management server provides the captured video and the data to a recipient designated by the user. The content management server verifies that the recipient is performing the movement by comparing data regarding the recipient during play of the captured video to the data associated with the captured video.

BRIEF DESCRIPTION OF THE DRAWINGS

FIG. 4 is a block level diagram of an exemplary user device that may be used to capture movement data.

DETAILED DESCRIPTION

Embodiments of the present invention include systems and methods for sharing movement data. A user device associated with a user is in communication with a content management server. The content management server receives data from the user device captured during a movement by the user in a real-world environment. The content management server renders a corresponding movement by a virtual character within a virtual environment based on the data. The content management server captures video of the corresponding movement within the virtual reality environment associated with the data. The content management server provides the captured video and the data to a recipient designated by the user. The content management server verifies that the recipient is performing the movement by comparing data regarding the recipient during play of the captured video to the data associated with the captured video.

Figure 1:
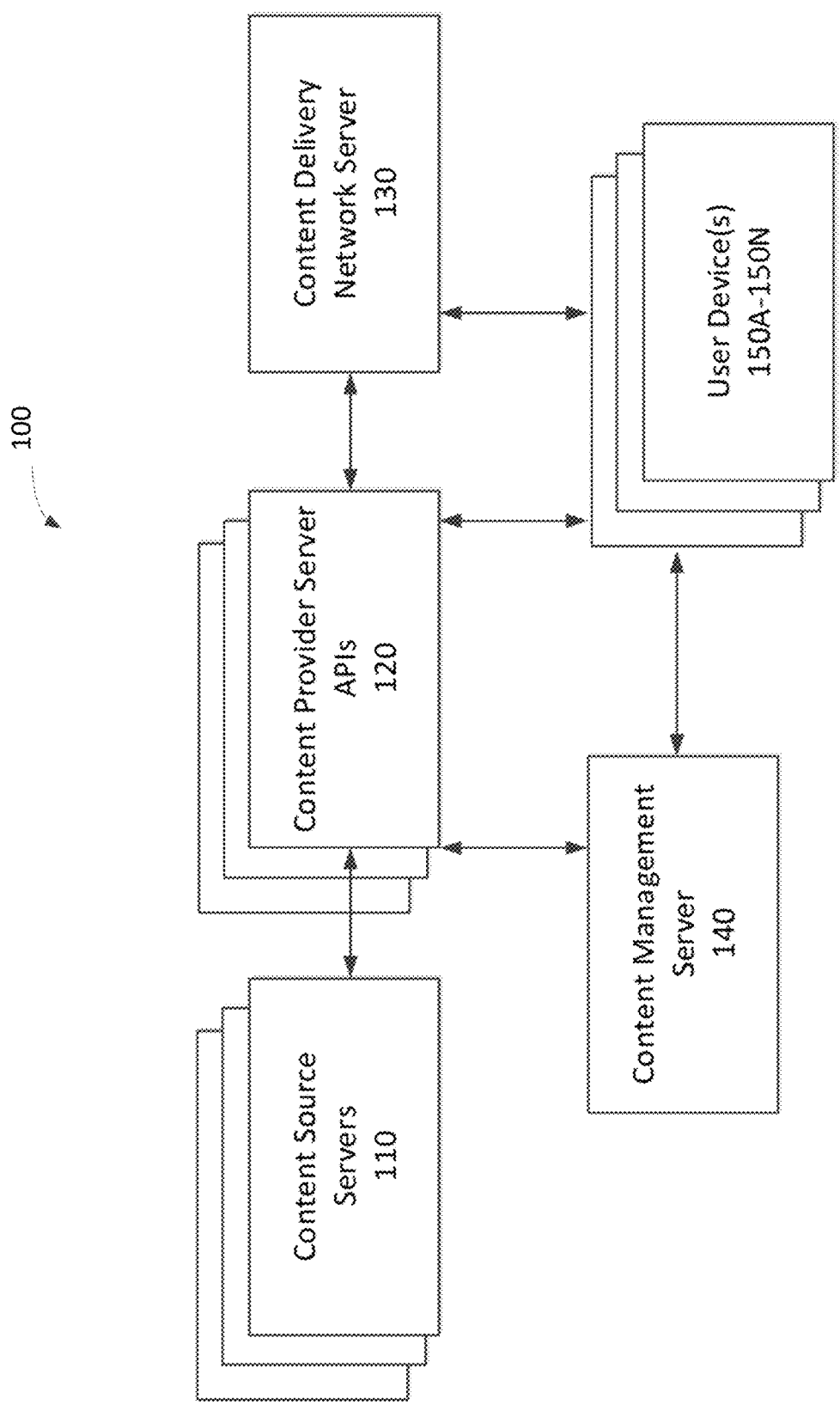
FIG. 1 illustrates an exemplary network environment in which a system for analyzing and sharing movement data may be implemented.

FIG. 1 illustrates an exemplary network environment in which a system for analyzing and sharing movement data may be implemented. The network environment 100 may include one or more content source servers 110 that provide digital content (e.g., games, other applications and services) for distribution, one or more content provider server application program interfaces (APIs) 120, content delivery network server 130, a content management server 140, and one or more user devices 150A-150N.

The servers described herein may include any type of server as is known in the art, including standard hardware computing components such as network and media interfaces, non-transitory computer-readable storage (memory), and processors for executing instructions or accessing information that may be stored in memory. The functionalities of multiple servers may be integrated into a single server. Any of the aforementioned servers (or an integrated server) may take on certain client-side, cache, or proxy server characteristics. These characteristics may depend on the particular network placement of the server or certain configurations of the server. Each server and device may communicate with each other via local or wide area communication networks, inclusive of cloud and Internet implementations.

Content source servers 110 may maintain and provide a variety of digital content available for distribution. The content source servers 110 may be associated with any content provider that makes its content available for access over a communication network. Such content may include not only digital video and games, but also other types of digital applications and services. Such applications and services may include any variety of different digital content and functionalities that may be provided to user devices 150. An example of content source servers 110 may be an Internet website that provides downloadable content and/or streaming content. The content provided by the content source servers 110 can include any type of multimedia content, such as movies, games, static/dynamic content, pictures, social media content, social media websites, virtual reality, augmented reality, mixed reality, etc. The user device 150 may include a plurality of different types of computing devices or computing systems known in the art. In some embodiments, content data is transmitted from the content source servers 110 to a user device 150, where the content data is then rendered by the user device 150 (or associated peripheral) in a format suitable for use by user device 150.

The digital content from content source server 110 may be provided through a content provider server API 120, which allows various types of content sources server 110 to communicate with other servers in the network environment 100 (e.g., user devices 150). The content provider server API 120 may be specific to the particular language, operating system, protocols, etc. of the content source server 110 providing the content, as well as the user devices 150. In a network environment 100 that includes multiple different types of content source servers 110, there may likewise be a corresponding number of content provider server APIs 120 that allow for various formatting, conversion, and other cross-device and cross-platform communication processes for providing content and other services to different user devices 150, which may use different operating systems, protocols, etc., to process such content. As such, applications and services in different formats may be made available so as to be compatible with a variety of different user device 150.

The content provider server API 120 may further facilitate access of each of the user devices 150 to the content hosted or services provided by the content source servers 110, either directly or via content delivery network server 130. Additional information, such as metadata, about the accessed content or service can also be provided by the content provider server API 120 to the user device 150. As described below, the additional information (i.e. metadata) can be usable to provide details about the content or service being provided to the user device 150. In some embodiments, the services provided from the content source servers 110 to the user device 150 via the content provider server API 120 may include supporting services that are associated with other content or services, such as chat services, ratings, and profiles that are associated with a particular game, team, community, etc. In such cases, the content source servers 110 may also communicate with each other via the content provider server API 120.

The content delivery network server 130 may include a server that provides resources, files, etc., related to the content from content source servers 110, including various content and service configurations, to user devices 150. The content delivery network server 130 can also be called upon by the user devices 150 that request to access specific content or services. Content delivery network server 130 may include universe management servers, game servers, streaming media servers, servers hosting downloadable content, and other content delivery servers known in the art.

Content management server 140 may include any data server known in the art that is capable of receiving data from the user device 150. The content rendered by the content management server 140 can be for essentially any type of computer application, and may include one or more types of content such as game, movie, audio, images, multimedia, among others. In some embodiments, the content, or portions thereof, is generated by the content management server 140. In some embodiments, the content, or portions thereof, is streamed from content source server 110 over one or more communication networks to the user device 150. In some embodiments, the content, or portions thereof, is streamed from a cloud gaming infrastructure over the communication network(s) to the user device 150. The infrastructure may direct various types of content to be transmitted from the content source servers 110 over the communication network(s) to the user device 150.

In exemplary embodiments, content management server 140 may specifically manage data exchanges related to movement of the user in the real-world physical space. Such data may be captured by a variety of user devices 150 (and/or associated sensors) associated with the user. The movement data may further be supplemented and enriched with analytical data, as well as data regarding the virtual or otherwise digital environment in which an associated player or character is located when the user performed the movement in the real-world.

In various embodiments, the content management server 140 may also engage a social media application to access one or more social media graphs the user in order to identify social contacts of the user. In some embodiments, the enriched movement data may be shared with other users that may not be social contacts or socially associated with the user in one or more existing social networks, but who may have played one or more video games with the user. The friend listing can include additional information about the user's friends, such as depicting games which are owned by each friend, identifying an online status of the friend (e.g. online, offline, inactive, etc.), the friend's last login and its duration, the last game played by the friend, etc. The social network includes user data, which includes data such as user's social graphs, posts, pictures, videos, biographical information, etc.

In an exemplary implementation, the user may provide input commands to the user device(s) 150 regarding capture of a movement in the real-world. Such commands may be given verbally, gesturally, or through other hardware or software-based user interfaces (e.g., buttons). In response to such commands, a camera (e.g., camera 404 of FIG. 4) and other sensors (e.g., motion detection system 418 of FIG. 4) on the user device 150 may be activated to capture images, video, and other types of data regarding the real-world environment in which the user is located. In some embodiments, the sensors may be distributed in the real-world environment to capture different perspectives and aspects of user movement. For example, some sensors may be worn (or held) on the body of the user, while other sensors may be stationary and located at different distance from the user, etc. The various sensors associated with user device 150 may be provided to content management server 140 for analysis and enrichment.

The content management server 140 may operate to analyze the images, video, sensor data, etc., captured by the sensors to generate metadata and various metrics characterizing the movement being performed by the user. The analysis and resulting metrics may break down the movement into a series of sub-movements, as well as characterizing the overall movement and sub-movements. Each movement (and sub-movement) may be characterized by metadata regarding the series and order of sub-movements, where each movement (and sub-movements) occur within the virtual environment and in interaction with virtual elements thereof, and other parameters that may be input by the user. For example, the user may specify that such movement be associated with custom audio-visual effects in the digital environment (e.g., associating a specified sub-movement with certain visual effects or sounds in the virtual environment). The user may also specify that the same movement (or sub-movement) be associated with different audio-visual effects if performed in different locations or under different conditions in the virtual environment.

In addition, metrics may be generated to characterize the movement. For example, metrics regarding the specific mechanics, rhythm, tempo, force, and other characteristics of each movement (and sub-movement) may be generated based on analyzing the combination of sensor data from different sensors used to capture movement data. Computer vision may be used to analyze images and video of the movement, and the resulting metrics may further be combined with other types of sensor data to generate additional metrics characterizing the movement. For example, analyzing the images and video of the movement may identify various locations, angles, shapes, etc., of different body parts in relation to each other and to the ground (or other features of the physical space) during each movement (and sub-movement). In addition, elements of timing, rhythm, and tempo may be evaluated for each movement and sub-movement in relation to each other. Other types of sensor data may further be used to generate metrics regarding a force with which each movement or sub-movement is performed. The initial movement data as captured by the sensors may be combined with the generated metadata and metrics within a movement profile (or other type of shareable content). The user may further attach custom names, parameters, and other preferences before sharing with other users (associated with user accounts and user devices).

The camera (discussed in further detail in relation to FIG. 4) of user device 150 can be configured to include multiple image capture devices, such as a stereoscopic pair of cameras, an infrared camera, a depth camera, or combinations thereof. In some embodiments, one or microphones (also discussed in further detail in relation to FIG. 4) can be used to capture sound from the user and/or from the environment in which the user device 150 is located.

In some embodiments, the user device 150 is configured to execute games locally on the processing hardware of the computing device. The games or content can be obtained in any form, such as physical media form (e.g., digital discs, tapes, cards, thumb drives, solid state chips or cards, etc.) or by way of download from the Internet (or other communication network). In some embodiments, the user device 150 functions as a client in communication over one or more communication networks with the cloud gaming infrastructure. The cloud gaming infrastructure may maintain and execute a video game being played by the user device 150. The computing device can be defined to transmit inputs received from the user device 150, the controller, and the camera, to the cloud gaming infrastructure, which processes the inputs to affect the game state of the executing video game.

Game data from a video game, such as video data, audio data, and tactile feedback data, can be transmitted from the content source servers 110 to the user devices 150. The computer system may further process the game data before transmission to the appropriate device, or may directly transmit the game data to the appropriate device. For example, video and audio streams may be transmitted to the user devices 150.

In some embodiments, the user device 150 may be associated with server that provides an internal service (e.g., to other servers) in network environment 100. In such cases, user device 150 may correspond to one of the content source servers 110 described herein. Alternatively, the user device 150 may be a client device that may include any number of different gaming consoles, mobile devices, laptops, and desktops. Such user devices 150 may also be configured to access data from other storage media, such as, but not limited to memory cards or disk drives as may be appropriate in the case of downloaded services. Such user devices 150 may include standard hardware computing components such as, but not limited to network and media interfaces, non-transitory computer-readable storage (memory), and processors for executing instructions that may be stored in memory. These user devices 150 may also run using a variety of different operating systems (e.g., iOS, Android), applications or computing languages (e.g., C++, JavaScript). An exemplary client device 150 is described in detail herein with respect to FIG. 4. Each user device 150 may be associated with participants or other types of spectators of a collection of digital content streams.

The user device 150 may also include a module configured to receive inertial sensor data from inertial sensors within the user device 150. The inertial sensor data indicates movement of the user device 150 in accordance with movement of a user by whom the user device 150 is associated with. The movement of the user is based on a virtual reality scene displayed within the user device 150. A route of movement of the user device 150 can be determined from inertial sensor data and a rate of movement of the user device 150. In some embodiments, the route of movement of the head mounted display corresponds to one or more user movements within a set of user movements including a forward lean, a backward lean, a left lean, a right lean, a left head turn, a right head turn, an upward head tilt, a downward head tilt, a squat, and a jump. However, in other embodiments, the route of movement of the head mounted display may correspond to essentially any user movement within the movement capabilities of the human body.

In some embodiments, the user device 150 can be used to manipulate, e.g., grab, move, push, pull, etc., a virtual object in a virtual reality (VR) or an augmented reality (AR) scene, which is displayed on the user device 150 or on another computing device, e.g., a television, a computer, etc. A virtual hand within a game moves when the user moves his/her hand while wearing the user device 150. Moreover, fingers of a virtual hand in the game move when the user moves his/her fingers while wearing the user device 150. Position and/or orientation of the fingers are determined from image data captured using the cameras described above and in FIG. 4 to generate the movement of fingers of the virtual hand.

A user's avatar may be automatically transformed from a single digital image into an animated 3D avatar. In particular, the user can upload a digital image or other image on the user device 150 and receive one or more avatars featuring different facial expressions and/or animations in return. The avatar is displayed to the user to be used as any still or animated image (for example, in GIF format). For example, the avatar can be sent to other users via SMS, MMS, e-mail messages, chats (e.g., Facebook Messenger), instant messengers (e.g., Skype or Windows Messenger), Twitter, Tik-Tok, blogs, forums or other means of electronic communication in purpose of sharing with one or more other individuals.

In some embodiments, the avatar may be realistically based on the user (e.g., having similar facial features, clothing, and body shape). In other embodiments, the avatar may be intentionally unrealistic, for example by mapping the movements of the user to facial features of a celebrity, a movie star, a politician, a video game character, or another user. The avatar may be an amalgam of realistic elements and intentionally unrealistic elements—for example, the face of the user may be used in the avatar, but the avatar may be given different clothing or a different body shape. Alternately, body of the user may be used in the avatar, but the avatar may be given the face of a celebrity, a movie star, a politician, a video game character, or another user.

The display of the user device 150 may generate a three-dimensional scene incorporating an avatar into virtual space or virtual environment with virtual interactive objects. The content management server 140 receives visual and/or distance information about the user captured by the user device 150. The content management server 140 extracts movement information describing movement of the user. The movement information can be encoded so as to describe movement of a "skeleton" of the user that is made up of key points within the user's body. The content management server 140 may allow augmentation of content by allowing introduction of user-related information, such as a user's avatar, identifier, representative image, etc., into the VR space presented at the user device 150A-150N of the users.

A second user of a second user device 150B may be a recipient designated by the user. The user device 150A transmits the information describing movements of the user and/or movements of the corresponding avatar to a second user device 150B or to the content management server 140 that then sends this information on to the second user device 150B, so that the second user device 150B can generate a scene featuring accurate movements by the avatar. The user device 150A receives information describing movements of the second user and/or movements of the corresponding second avatar, from the second user device 150B, or from an intermediary device such as the content management server 140 that then sends this information on to first user device 150A as it was received from the second user device 150B, so that the first user device 150A can generate a scene featuring accurate movements by the second avatar.

In some embodiments, the movement profile may be applied to data regarding the recipient. For example, the recipient of the movement profile may play video or view images of the movement via a corresponding user device 150, which may be presented in combination with the enriching metadata and metrics. When the recipient is ready to attempt or otherwise perform the movement, data regarding the recipient may be captured and compared to the movement profile. Similar analytics and metrics may be generated regarding the recipient and compared to the corresponding analytics and metrics in the movement profile. Where the analytics and metrics match within one or more predetermined thresholds, the recipient may be verified as having performed the movement correctly. In some embodiments, such verification may result in certain notifications or audio-visual effects in the virtual environment.

In some embodiments of the present invention, where the movement by the recipient may not result in analytics or metrics that come within the predetermined threshold(s), the differences may be identified and used to provide guidance to the recipient. For example, where a particular movement or sub-movement is performed too slowly or with too little force, the recipient may be provided with a notification to move faster or with more force respectively, as well as side-by-side videos of the original movement indicated by the movement profile and video of the recipient. Similarly, where the recipient is creating different shapes or angles with their body than indicated by the movement profile, the recipient may be provided a notification with an image of the shape or angle specified by the movement profile superimposed over an image of the recipient. Thus, the recipient may learn exactly how their own movements differ from that characterized by the movement profile.

The user device 150 or computing device generates a representation of the movements of the user as captured and has the avatar perform the generated representation of the movements of the user. The user device 150 also generates a representation of the movements of the second user as received and has the second avatar perform the generated representation of the movements of the second user. The user device 150 also updates the virtual space or environment and any virtual interactive objects as appropriate.

Figure 2:
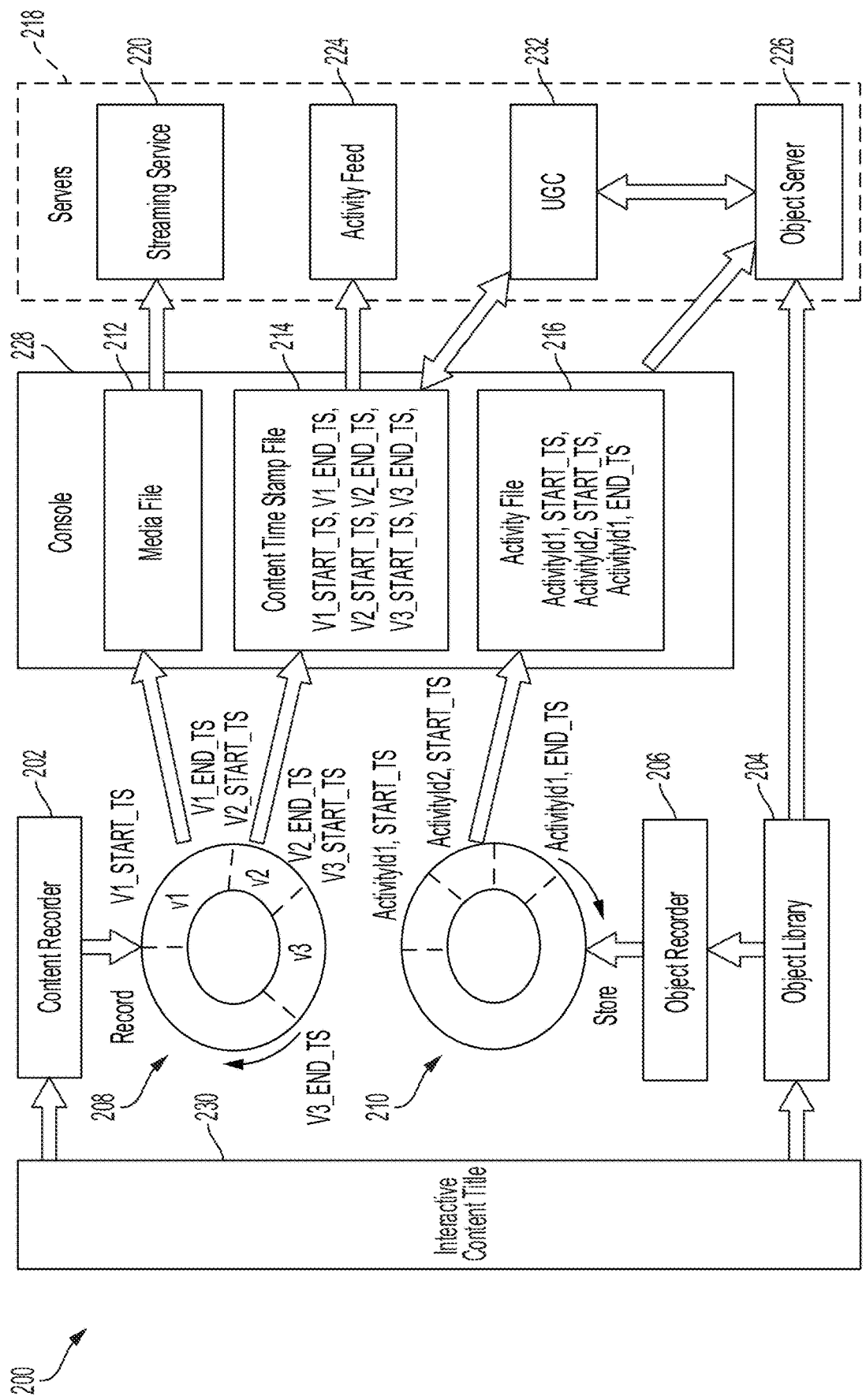
FIG. 2 illustrates an exemplary uniform data system (UDS) that may be used to analyze movement data in relation to virtual environments.

FIG. 2 illustrates an exemplary uniform data system (UDS) that may be used to analyze movement data in relation to virtual environments. Based on data provided by UDS, content management server 140 can be made aware of what in-game objects, entities, activities, and events that users have engaged with, and thus support analysis of and coordination with in-game activities. Each user interaction may be associated the metadata for the type of in-game interaction, location within the in-game environment, and point in time within an in-game timeline, as well as other players, objects, entities, etc., involved. Thus, metadata can be tracked for any of the variety of user interactions that can occur in during a game session, including associated activities, entities, settings, outcomes, actions, effects, locations, and character stats. Such data may further be aggregated, applied to data models, and subject to analytics. Such a UDS data model may be used to assign contextual information to each portion of information in a unified way across games.

As illustrated in FIG. 2, an exemplary console 228 (e.g., a user device 130) and exemplary servers 218 (e.g., streaming server 220, an activity feed server 224, an user-generated content (UGC) server 232, and an object server 226) are shown. In one example, the console 228 may be implemented on the platform server 120, a cloud server, or on any of the servers 218. In an exemplary example, a content recorder 202 may be implemented on the platform server 120, a cloud server, or on any of the servers 218. Such content recorder 202 receives and records content (e.g., media) from an interactive content title 230 onto a content ring-buffer 208. Such ring-buffer 208 may store multiple content segments (e.g., v1, v2 and v3), start times for each segment (e.g., V1_START_TS, V2_START_TS, V3_START_TS), and end times for each segment (e.g., V1_END_TS, V2_END_TS, V3_END_TS). Such segments may be stored as a media file 212 (e.g., MP4, WebM, etc.) by the console 228. Such media file 212 may be uploaded to the streaming server 220 for storage and subsequent streaming or use, though the media file 212 may be stored on any server, a cloud server, any console 228, or any user device 130. Such start times and end times for each segment may be stored as a content time stamp file 214 by the console 228. Such content time stamp file 214 may also include a streaming ID, which matches a streaming ID of the media file 212, thereby associating the content time stamp file 214 to the media file 212. Such content time stamp file 214 may be uploaded and stored to the activity feed server 224 and/or the UGC server 232, though the content time stamp file 214 may be stored on any server, a cloud server, any console 228, or any user device 130.

Concurrent to the content recorder 202 receiving and recording content from the interactive content title 230, an object library 204 receives data from the interactive content title 230, and an object recorder 206 tracks the data to determine when an object beings and ends. The object library 204 and the object recorder 206 may be implemented on the platform server 120, a cloud server, or on any of the servers 218. When the object recorder 206 detects an object beginning, the object recorder 206 receives object data (e.g., if the object were an activity, user interaction with the activity, activity ID, activity start times, activity end times, activity results, activity types, etc.) from the object library 204 and records the activity data onto an object ring-buffer 210 (e.g., ActivityID1, START_TS; ActivityID2, START_TS; ActivityID3, START_TS). Such activity data recorded onto the object ring-buffer 210 may be stored in the object file 216. Such object file 216 may also include activity start times, activity end times, an activity ID, activity results, activity types (e.g., competitive match, quest, task, etc.), user or peer data related to the activity. For example, an object file 216 may store data regarding an item used during the activity. Such object file 216 may be stored on the object server 226, though the object file 216 may be stored on any server, a cloud server, any console 228, or any user device 130.

Such object data (e.g., the object file 216) may be associated with the content data (e.g., the media file 212 and/or the content time stamp file 214). In one example, the UGC server 232 stores and associates the content time stamp file 214 with the object file 216 based on a match between the streaming ID of the content time stamp file 214 and a corresponding activity ID of the object file 216. In another example, the object server 226 may store the object file 216 and may receive a query from the UGC server 232 for an object file 216. Such query may be executed by searching for an activity ID of an object file 216 that matches a streaming ID of a content time stamp file 214 transmitted with the query. In yet another example, a query of stored content time stamp files 214 may be executed by matching a start time and end time of a content time stamp file 214 with a start time and end time of a corresponding object file 216 transmitted with the query. Such object file 216 may also be associated with the matched content time stamp file 214 by the UGC server 232, though the association may be performed by any server, a cloud server, any console 228, or any user device 130. In another example, an object file 216 and a content time stamp file 214 may be associated by the console 228 during creation of each file 216, 214.

Figure 3:
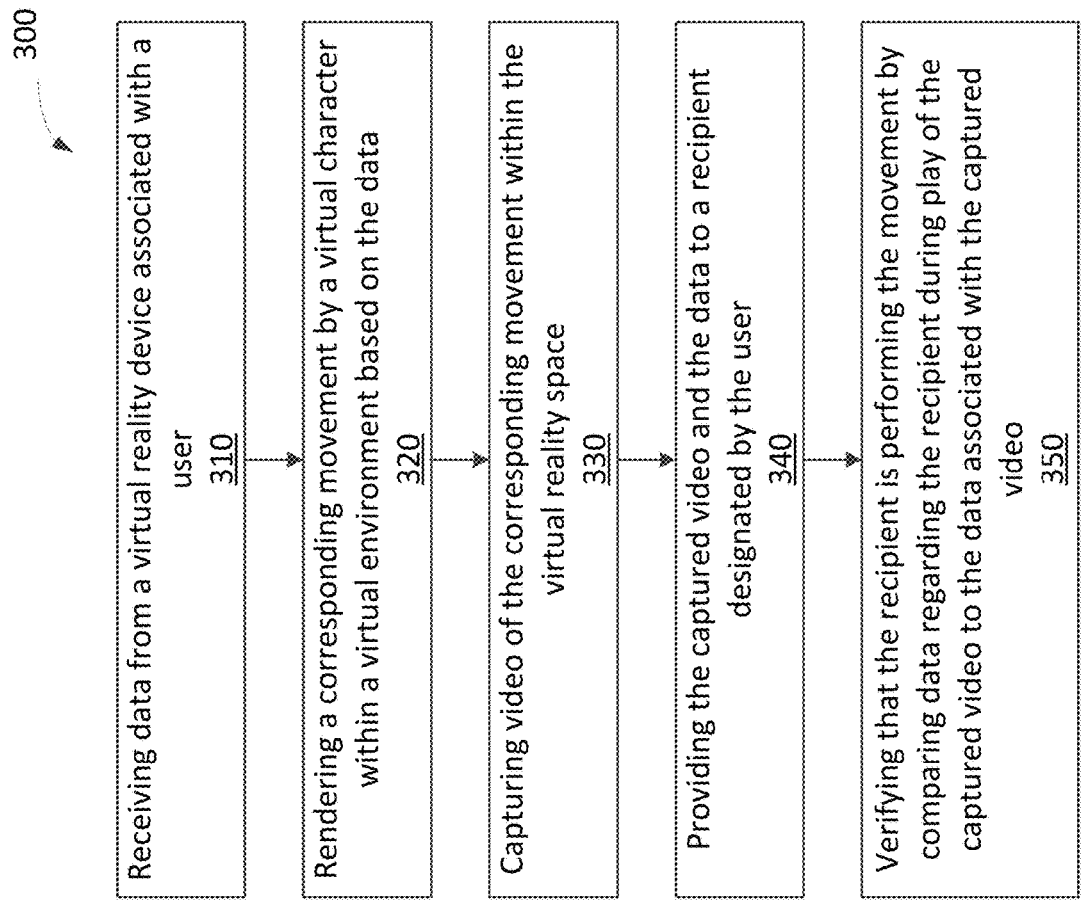
FIG. 3 is a flowchart illustrating an exemplary method for analyzing and sharing movement data.

FIG. 3 is a flowchart illustrating an exemplary method for analyzing and sharing movement data. The method 300 of FIG. 3 may be embodied as executable instructions in a non-transitory computer readable storage medium including but not limited to a CD, DVD, or non-volatile memory such as a hard drive. The instructions of the storage medium may be executed by a processor (or processors) to cause various hardware components of a computing device hosting or otherwise accessing the storage medium to effectuate the method. The steps identified in FIG. 3 (and the order thereof) are exemplary and may include various alternatives, equivalents, or derivations thereof including but not limited to the order of execution of the same.

At step 310, data from a user device associated with a user is received. The data is captured during a movement by the user in a real-world environment. The movement by the user in the real-world environment may be indicated by real-world environment data captured by the user device 150. The data may be image data captured by the camera of the user device 150. In another embodiment, the data may be captured by inertial sensors on the user device 150. The real-world environment data along with the one or more images and the image data of the user interacting in the real-world environment captured the user device 150 may be forwarded to the content management server 140.

At step 320, a corresponding movement by a virtual character within a virtual environment based on the data is rendered. At step 330, video of the corresponding movement within the virtual reality environment is captured. The captured video is associated with the data. In an embodiment, video of the corresponding movement within the virtual reality environment is captured when the data meets a predetermined threshold.

At step 340, the captured video and the data is provided to a recipient designated by the user. The captured video and the data may be provided to the recipient through one or more social networks associated with the user and the recipient.

At step 350, it is verified that the recipient is performing the movement by comparing data regarding the recipient during play of the captured video to the data associated with the captured video. A selection of inputs by the user, via the user device 150, may be received for performing a different movement within the virtual environment. An update to the rendering of the virtual reality environment may be generated to reflect implementation of the different movement. A signature movement associated with the user may be created based on the data meeting the predetermined threshold.

FIG. 4 is a block diagram of an exemplary electronic entertainment system 400. The entertainment system 400 of FIG. 4 includes a main memory 405, a central processing unit (CPU) 410, vector unit 415, a graphics processing unit 420, an input/output (I/O) processor 425, an I/O processor memory 430, a controller interface 435, a memory card 440, a Universal Serial Bus (USB) interface 445, and an IEEE interface 450. The entertainment system 400 further includes an operating system read-only memory (OS ROM) 455, a sound processing unit 460, an optical disc control unit 470, and a hard disc drive 465, which are connected via a bus 475 to the I/O processor 425.

FIG. 4 is a block level diagram of an exemplary user device 400 that may be used to capture movement data. It should be understood that more or less components can be included or excluded from the user device 400 than what is shown in FIG. 4, depending on the configuration and functions enabled. The user device 400 may include a processor 402 for executing program instructions. A memory 406 is provided for data storage purposes, and may include both volatile and non-volatile memory. A display 416 is included which provides a visual interface that a user may view. The display 416 can be defined by one single display, or in the form of a separate display screen for each eye. When two display screens are provided, it is possible to provide left-eye and right-eye video content separately. Separate presentation of video content to each eye, for example, can provide for better immersive control of three-dimensional content of the virtual reality scene.

A motion detection module 418 may include any of various kinds of motion sensitive hardware, such as a magnetometer 420, an accelerometer 424, and a gyroscope 426. The user device 400 may be equipped with inertial sensors 422 configured to generate inertial sensor data indicating movement of the user device 400 in accordance with movement of the user with which the user device 400 is associated. The magnetometer 420 measures the strength and direction of the magnetic field in the vicinity of the user device 500. In some embodiments, three magnetometers 420 are used within the user device 400, ensuring an absolute reference for the world-space yaw angle. In some embodiments, the magnetometer 520 is designed to span the Earth's magnetic field, which is ±80 microtesla. Magnetometers are affected by metal, and provide a yaw measurement that is monotonic with actual yaw. The magnetic field may be warped due to metal in the environment, which causes a warp in the yaw measurement. If necessary, this warp can be calibrated using information from other sensors such as the gyroscope or the camera. In some embodiments, the accelerometer 424 is used together with the magnetometer 420 to obtain the inclination and azimuth of the user device 400.

In some embodiments, the present invention can also include one or more external inertial sensors positioned on the body of the user. The present invention may include an operation for comparing the external inertial sensor data to the inertial sensor data received from the inertial sensors 422 in the user device 400 in order to determine a specific movement made by the user.

The accelerometer 424 is a device for measuring acceleration and gravity induced reaction forces. Single and multiple axis (e.g., six-axis) models are able to detect magnitude and direction of the acceleration in different directions. The accelerometer 524 is used to sense inclination, vibration, and shock. In one embodiment, three accelerometers 524 are used to provide the direction of gravity, which gives an absolute reference for two angles (world-space pitch and world-space roll).

The gyroscope 426 is a device for measuring or maintaining orientation, based on the principles of angular momentum. In one embodiment, three gyroscopes 426 provide information about movement across the respective coordinate axes (x, y, and z) based on inertial sensing. The gyroscopes 426 help in detecting fast rotations. However, the gyroscopes 426 can drift overtime without the existence of an absolute reference. This requires resetting the gyroscopes 426 periodically, which can be done using other available information, such as positional/orientation determination based on visual tracking of an object, accelerometer, magnetometer, etc.

A camera 404 is provided for capturing images and image streams of the real-world environment to which the user device 400 is exposed. More than one camera 404 (optionally) may be included in the user device 400, including a camera 404 that is rear-facing (directed away from a user when the user is viewing the display of the user device 400), and a camera 404 that is front-facing (directed towards the user when the user is viewing the display of the user device 400). In some embodiments, a camera 404 may be included in the user device 400 for sensing depth information of objects in the real-world environment to which the user device 500 is exposed.

The user device 400 includes speakers 412 for providing audio output. Also, a microphone 414 may be included for capturing audio from the real-world environment, including sounds from the ambient environment, speech made by the user, etc.

A WiFi module 410 may be included for enabling connection of the user device 400 to the Internet via wireless networking technologies. Also, the user device 400 may include a Bluetooth module 408 for enabling wireless connection to other devices.

It should be understood that the components of the user device 400 as shown in FIG. 4 are examples of components that may be included in user device 400, and do not represent all possible components that can be included in the user device 400. For example, in various embodiments, the user device 400 may or may not include some of the components shown in FIG. 4. In some embodiments, the user device 400 may include additional components not shown in FIG. 4.

Figure 5:
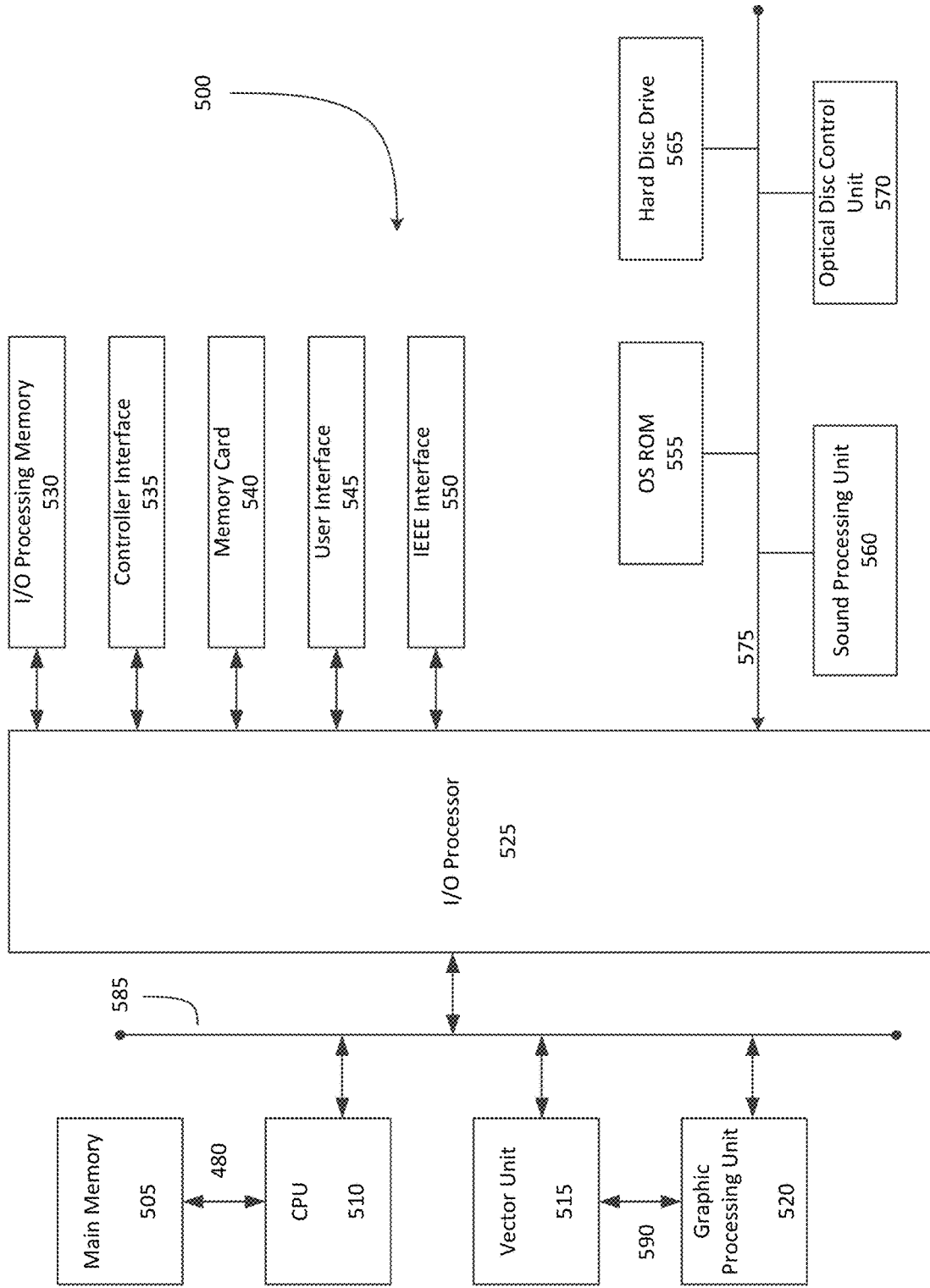
FIG. 5 is a block diagram of an exemplary electronic entertainment system that may be used in embodiments of the present invention.

FIG. 5 is a block diagram of an exemplary electronic entertainment system that may be used in embodiments of the present invention. Entertainment system 500 may be an electronic game console. Alternatively, the entertainment system 500 may be implemented as a general-purpose computer, a set-top box, a hand-held game device, a tablet computing device, or a mobile computing device or phone. Entertainment systems may contain more or less operating components depending on a particular form factor, purpose, or design.

The CPU 510, the vector unit 515, the graphics processing unit 520, and the I/O processor 525 of FIG. 5 communicate via a system bus 585. Further, the CPU 510 of FIG. 5 communicates with the main memory 505 via a dedicated bus 580, while the vector unit 515 and the graphics processing unit 520 may communicate through a dedicated bus 590. The CPU 510 of FIG. 5 executes programs stored in the OS ROM 555 and the main memory 505. The main memory 505 of FIG. 5 may contain pre-stored programs and programs transferred through the I/O Processor 525 from a CD-ROM, DVD-ROM, or other optical disc (not shown) using the optical disc control unit 570. I/O Processor 525 of FIG. 5 may also allow for the introduction of content transferred over a wireless or other communications network (e.g., 4G, LTE, 3G, and so forth). The I/O processor 525 of FIG. 5 primarily controls data exchanges between the various devices of the entertainment system 500 including the CPU 510, the vector unit 515, the graphics processing unit 520, and the controller interface 535.

The graphics processing unit 520 of FIG. 5 executes graphics instructions received from the CPU 510 and the vector unit 515 to produce images for display on a display device (not shown). For example, the vector unit 515 of FIG. 5 may transform objects from three-dimensional coordinates to two-dimensional coordinates, and send the two-dimensional coordinates to the graphics processing unit 520. Furthermore, the sound processing unit 560 executes instructions to produce sound signals that are outputted to an audio device such as speakers (not shown). Other devices may be connected to the entertainment system 500 via the USB interface 545, and the IEEE 1394 interface 550 such as wireless transceivers, which may also be embedded in the system 500 or as a part of some other component such as a processor.

A user of the entertainment system 500 of FIG. 5 provides instructions via the controller interface 535 to the CPU 510. For example, the user may instruct the CPU 510 to store certain game information on the memory card 540 or other non-transitory computer-readable storage media or instruct a character in a game to perform some specified action.

The present invention may be implemented in an application that may be operable by a variety of end user devices. For example, an end user device may be a personal computer, a home entertainment system (e.g., Sony PlayStation2® or Sony PlayStation3® or Sony PlayStation4®), a portable gaming device (e.g., Sony PSP® or Sony Vita®), or a home entertainment system of a different albeit inferior manufacturer. The present methodologies described herein are fully intended to be operable on a variety of devices. The present invention may also be implemented with cross-title neutrality wherein an embodiment of the present system may be utilized across a variety of titles from various publishers.

The present invention may be implemented in an application that may be operable using a variety of devices. Non-transitory computer-readable storage media refer to any medium or media that participate in providing instructions to a central processing unit (CPU) for execution. Such media can take many forms, including, but not limited to, non-volatile and volatile media such as optical or magnetic disks and dynamic memory, respectively. Common forms of non-transitory computer-readable media include, for example, a floppy disk, a flexible disk, a hard disk, magnetic tape, any other magnetic medium, a CD-ROM disk, digital video disk (DVD), any other optical medium, RAM, PROM, EPROM, a FLASHEPROM, and any other memory chip or cartridge.

Various forms of transmission media may be involved in carrying one or more sequences of one or more instructions to a CPU for execution. A bus carries the data to system RAM, from which a CPU retrieves and executes the instructions. The instructions received by system RAM can optionally be stored on a fixed disk either before or after execution by a CPU. Various forms of storage may likewise be implemented as well as the necessary network interfaces and network topologies to implement the same.

The foregoing detailed description of the technology has been presented for purposes of illustration and description. It is not intended to be exhaustive or to limit the technology to the precise form disclosed. Many modifications and variations are possible in light of the above teaching. The described embodiments were chosen in order to best explain the principles of the technology, its practical application, and to enable others skilled in the art to utilize the technology in various embodiments and with various modifications as are suited to the particular use contemplated. It is intended that the scope of the technology be defined by the claim.

What is claimed is:

1. A method for sharing movement data, the method comprising:
    receiving sensor data from one or more sensors associated with a user during an interactive session, wherein the sensor data is captured during a movement by the user in a real-world environment;
    analyzing the sensor data to generate metadata characterizing the movement as a series of sub-movements;
    receiving user input specifying that one or more of the sub-movements is associated with a specified audio-visual effect in a virtual environment of the interactive session;
    rendering a corresponding movement by a virtual character within the virtual environment based on the sensor data;
    capturing video of the corresponding movement within the virtual environment, wherein the captured video is associated with the sensor data;
    providing a movement profile that includes the captured video and the specified audio-visual effect associated with the specified sub-movements characterized by the metadata generated from the sensor data to a recipient device of a recipient designated by the user; and
    verifying that the recipient is performing the specified sub-movements by comparing data regarding the recipient during play of the captured video to the sensor data associated with the captured video within the movement profile, wherein the specified audio-visual effect occurs in the virtual environment based on the verification.

2. The method of claim 1, wherein the movement profile further includes custom parameters specified by the user, wherein the custom parameters include one or more virtual elements of the virtual environment.

3. The method of claim 2, further comprising generating video of the recipient within the virtual environment as the recipient is performing the movement, and updating the virtual environment with the virtual elements associated with the custom parameters based on the verification.

4. The method of claim 1, wherein the sensor data includes image data or video data of the movement by the user in the real-world environment, and further comprising applying computer vision to the image data or video data to generate metadata or metrics.

5. The method of claim 1, wherein verifying that the recipient is performing the specified sub-movements is based on one or more matches of the data regarding the recipient to the movement profile that are within a predetermined threshold.

6. The method of claim 1, further comprising analyzing the data regarding the recipient to identify one or more differences to the movement profile, and generating a notification to the recipient regarding the identified differences.

7. The method of claim 1, further comprising superimposing one or more images from the movement profile over one or more images of the recipient, and providing the superimposed images to the recipient device.

8. The method of claim 1, wherein the movement profile further specifies one or more conditions of the virtual environment.

9. The method of claim 8, wherein verifying that the recipient is performing the specified sub-movements is based on one or more matches to the specified conditions of the virtual environment.

10. A system for sharing movement data, the system comprising:
    a sensor interface that receives sensor data from one or more sensors associated with a user during an interactive session, wherein the sensor data is captured during a movement by the user in a real-world environment;
    a processor that executes instructions stored in memory, wherein the processor executes the instructions to:
        analyzes the sensor data to generate metadata characterizing the movement as a series of sub-movements;
        receives user input specifying that one or more of the sub-movements is associated with a specified audio-visual effect in a virtual environment of the interactive session;
        render a corresponding movement by a virtual character within the virtual environment based on the sensor data, and
        capture video of the corresponding movement within the virtual environment, wherein the captured video is associated with the sensor data; and
    a communication interface that provides a movement profile that includes the captured video and the specified audio-visual effect associated with the specified sub-movements characterized by the metadata generated from the sensor data to a recipient device of a recipient designated by the user, wherein the recipient is verified as performing the specified sub-movements based on comparing data regarding the recipient during play of the captured video to the sensor data associated with the captured video within the movement profile, and wherein the specified audio-visual effect occurs in the virtual environment based on the verification.

11. The system of claim 10, wherein the movement profile further includes custom parameters specified by the user, wherein the custom parameters include one or more virtual elements of the virtual environment.

12. The system of claim 11, wherein the processor executes further instructions to generate video of the recipient within the virtual environment as the recipient is performing the movement, and updating the virtual environment with the virtual elements associated with the custom parameters based on the verification.

13. The system of claim 10, wherein the sensor data includes image data or video data of the movement by the user in the real-world environment, and wherein the processor executes further instructions to apply computer vision to the image data or video data to generate metadata or metrics.

14. The system of claim 10, wherein the recipient is verified as performing the specified sub-movements based on one or more matches of the data regarding the recipient to the movement profile that are within a predetermined threshold.

15. The system of claim 10, wherein the processor executes further instructions to analyze the data regarding the recipient to identify one or more differences to the movement profile, and to generate a notification to the recipient regarding the identified differences.

16. The system of claim 10, wherein the processor executes further instructions to superimpose one or more images from the movement profile over one or more images of the recipient, and wherein the communication interface provides the superimposed images to the recipient device.

17. The system of claim 10, wherein the movement profile further specifies one or more conditions of the virtual environment.

18. The system of claim 17, wherein the recipient is verified as performing the specified sub-movements based on one or more matches to the specified conditions of the virtual environment.

19. A non-transitory, computer-readable storage medium, having embodied thereon a program executable by a processor to perform a method for sharing movement data, the method comprising:

receiving sensor data from one or more sensors associated with a user during an interactive session, wherein the sensor data is captured during a movement by the user in a real-world environment;

analyzing the sensor data to generate metadata characterizing the movement as a series of sub-movements;

receiving user input specifying that one or more of the sub-movements is associated with a specified audio-visual effect in a virtual environment of the interactive session;

rendering a corresponding movement by a virtual character within the virtual environment based on the sensor data;

capturing video of the corresponding movement within the virtual environment, wherein the captured video is associated with the sensor data;

providing a movement profile that includes the captured video and the specified audio-visual effect associated with the specified sub-movements characterized by the metadata generated from the sensor data to a recipient device of a recipient designated by the user; and verifying that the recipient is performing the specified sub-movements by comparing data regarding the recipient during play of the captured video to the sensor data associated with the captured video within the movement profile, wherein the specified audio-visual effect occurs in the virtual environment based on the verification.

* * * * *